US00PP12169P2

(12) United States Plant Patent
Bittner

(10) Patent No.: US PP12,169 P2
(45) Date of Patent: Oct. 30, 2001

(54) FRAGARIA PLANT NAMED 'FRANOR'

(75) Inventor: Walter Bittner, Willstattland (DE)

(73) Assignee: Blooms of Bressingham Ltd., Norfolk (GB)

( * ) Notice: Subject to any disclaimer, the term of this patent is extended or adjusted under 35 U.S.C. 154(b) by 0 days.

(21) Appl. No.: 09/198,508

(22) Filed: Nov. 24, 1998

(51) Int. Cl.[7] ..... A01H 5/00

(52) U.S. Cl. ..... Plt./208

(58) Field of Search ..... Plt./208, 209

(56) References Cited

U.S. PATENT DOCUMENTS

P.P. 8,801 * 6/1994 Ellis ..... Plt./208

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of strawberry plant named 'Franor' characterized by the large single bright red-purple flowers which bloom starting from mid-May and continuing through to early November or until the first frost, bushy clumps which spread out by runners to form a carpet of foliage, its 5 or 6 flower petals which are separately formed and normally spaced, and its versatility of use for border, ground covers, in tubs, or in hanging baskets.

1 Drawing Sheet

BACKGROUND OF THE INVENTION

The present invention relates to a new and distinct cultivar of strawberry plant named 'Franor'. Strawberry plants are hardy perennial herbaceous plants of the genus Fragaria, a member of the Rosaceae family.

The new cultivar is the result of a spontaneous mutation occurring on a plant of the parent cultivar 'Frel', disclosed in U.S. Plant Pat. No. 7,598. The new cultivar is a naturally occurring sport from Fragaria 'Frel'. The Genus is Fragaria, which is a member of the Rosaceae family. Fragaria 'Frel', from which the instant plant originated, is a cross between *Potentilla palustris* and *Fragaria grandiflora*. The mutation was discovered by the inventor Walter Bittner in Hamm, Federal Republic of Germany, with the mutative portion of the parent plant being removed from the parent plant, grown and observed. The much brighter red-purple flower color of the mutative portion of the plant was readily observable and led to the discovery.

The instant plant was first asexually reproduced by the inventor in Hamm, Federal Republic of Germany, by taking runners from the initially discovered mutation. This, along with subsequent generations of asexual reproduction, have clearly established that the new cultivar propagates true from generation to generation. The instant cultivar reproduces true to type, generation to generation.

The new cultivar is similar in many respects to the parent cultivar 'Frel'. The flower shape, foliage shape and color, and relatively minor production of fruit are similar for both cultivars. The primary difference between 'Franor' and 'Frel' is in flower color, with the flower petals of 'Franor' being a very bright red-purple (RHS 57A), compared to the much lighter, pinkish red-purple flower color of 'Frel'. In addition, there are 5 or 6 petals in 'Franor' which, when mature, tend to be spaced one from the other. By contract, 'Frel' has 6 or 7 petals which often overlap. Also, 'Franor' has 2 to 5 fewer stamens and the stamens also tend to be spaced further apart than the stamens of 'Frel'.

BRIEF DESCRIPTION OF THE INVENTION

The following characteristics in combination distinguish 'Franor' from the parent and other known cultivars of this type known to the inventor:

1. 'Franor' has achieved the aim of being a quality flowering perennial displaying quality foliage and flowers. The many large single bright red-purple flowers make an excellent display from mid-May to early November, or indeed till the first frost.

2. The new cultivar forms bushy clumps which will flower for many weeks starting mid-May through to early November under normal growing techniques in the United Kingdom. These clumps will spread out by runners, joining together to form a carpet of foliage. The obovate glossy semi-evergreen leaves make a green backdrop to the many large single bright red-purple flowers.

3. The plant thrives best in full sun and well-drained soil, although the plant will also tolerate partial shade.

4. The flowers are of a classic Fragaria flower shape, but 5–6 petals are formed which are clearly separate and spaced apart on mature flowers. The obovate glossy semi-evergreen leaves resemble those of 'Frel'.

5. As with 'Frel', 'Franor' produces only a small amount of edible strawberries, being grown primarily for its flowering properties. Only about 30% of the flowers of 'Franor' will produce fruit, similar to 'Frel'.

6. The new cultivar is very versatile, being used for borders, ground covers, in tubs, and in hanging baskets.

BRIEF DESCRIPTION OF THE DRAWING

The colored photographic sheet comprises a top view of a typical plant or 'Franor', showing flower and foliage characteristics.

DETAILED BOTANICAL DESCRIPTION

The following is a detailed description of the new cultivar, based on plants grown in Germany and England. Plants described were about one year old. All color determinations and comparisons are based on The Royal Horticultural Society (R.H.S.) Colour Chart. The plants were observed in Bressingham, England, under UK conditions. The plants were grown in 5 liter containers. The instant plant requires a pollinator and will not reproduce from seed.

Origin: A spontaneous mutation from Fragaria 'Frel'.
Habit: Low bushy clumps.
Size: Mature plants are 20 cm in height with a spread of 60 cm, spreading by runners.
Root system: Fibrous.
Plant vigor: A herbaceous perennial that shows vigorous and healthy growth throughout Great Britain. Plants raised from runners taken in July, fill 5 liter containers in 12 months. Propagation of plugs to 1 liter takes approximately 10 weeks. Normally, cuttings are taken in July, then over the winter, and potted to 1 liter in February, ready for sale in April.
Blooming habit: Abundant showy single red-purple flowers with yellow centers. The flowers are borne on cymes and are positioned well above the foliage. The flowers display clearly separate petals.
Blooming period: From mid-May continuing into early November or until the first frost.
Hardiness: Winter hardy throughout the British Isles and on Mainland Europe. Although the plant has not been fully tested for maximum summer tolerance, it has been grown above 32° C. (90° F.).
Pest and disease resistance: Fragaria 'Franor' shows no more suscepibility to pest and disease resistance than Fragaria 'Frel'; it has been grown over successive generations and has been found to be vigorous and healthy.

FOLIAGE

Arrangement: Compound with three leaflets.
Type: Semi-evergreen, with leaves dying back to ground in severe winters.
Texture: Smooth, glossy upper surface; hairy lower surface.
Length of individual leaflet: 2.5 to 5 cm.
Width of individual leaflet: 2 to 4 cm.
Whole leaf length: 6 cm.
Whole leaf width: 8 cm.
Petiole length: 5 to 8 cm.
Petiole diameter: 2 mm.
Petiole color: RHS yellow-green 145 C, maturing to RHS red 46 B.
Margins: Coursely serrate.
Apex: Obtuse.
Base: Cuneate.
Upper surface, mature leaves: RHS 137 A.
Lower surface, mature leaves: RHS 138 D.
Venation pattern: Pinnate.
Venation color: Upper surface is RHS yellow-green 145 B, Lower surface is RHS yellow-green 144 C.

FLOWERS

Petal count: 5 or 6 of similar size. Petals are clearly separate.
Petal shape: Orbicular.
Petal length: 15 mm.
Petal width: 13 mm.
Petal apex: Obtuse.
Petal base: Obtuse.
Petal margin: Broadly serrate to dentate.
Petal texture: Velvet-like.
Mature petal color: Upper surface is RHS red-purple 57 A, Lower surface is RHS red purple 60 B.
Immature petal color: Upper surface is RHS red 53A, Lower surface is RHS red-purple 60 C.
Fragrance: Slight fruity fragrance at flowering and when any fruit are set.
Flower type: Simple.
Flower size: 2 to 3 cm diameter.
Petiolule length: 1 cm to 2 cm.
Petiolule diameter: 1.5 mm.
Petiolule color: RHS yellow-green 146 C, maturing to RHS red 46 B.
Carpels: Numerous, glabrous, RHS 13 B.
Stamens: 20, RHS 13 B.
Anther shape: Round.
Anther size: 1 mm.
Anther color: RHS red 45 B on the edge; RHS yellow 13 B in the center, with a small amount of pollen RHS yellow-orange 15 B.
Pistils: Numerous, 60 to 80.
Stigma shape: Rounded.
Stigma color: RHS yellow 13 B.
Style length: 1 mm.
Style color: RHS yellow-orange 14 C.
Ovary size: 1 mm.
Ovary color: RHS greyed-yellow 160 B.
Stolon length: 60 cm.
Stolon diamenter: 2 mm to 3 mm.
Stolon color: RHS green 137A.

SEPALS

Length: 12 mm.
Width: 4 mm.
Shape: Subulate.
Number: 12.
Apex: Acute, fused at the base.
Color: Immature upper surface is RHS yellow-orange 14 B. Immature lower surface is RHS yellow-orange 14 B. Mature upper surface is RHS 145 B. Mature lower surface is RHS 145 B.
Margin: Entire.
Texture: Slightly hairy.

BUDS

Length: 10 mm.
Diameter: 9 mm.
Shape: Rounded.
Color: RHS red 53 A.

FRUIT

Length: 2 cm.
Diameter: 1.5 cm to 2 cm.
Weight: 5 to 10 grams per berry.
Color: RHS greyed-yellow 160 D as immature; RHS red-purple 59 A matured.
Achene position: Sunken into berry.
Achene color: RHS 46 A.
Production: 15 to 25 berries per plant per year.
Harvest: Small fruits will be produced from mid-July, about 9 weeks after first flowers observed.

Fruiting truss length: 2.5 cm.
Fruiting truss diameter: 1.5 cm.
Fruiting truss color: RHS red 46B.

I claim:

1. A new and distinct cultivar of strawberry plant named 'Franor', substantially as shown and described.

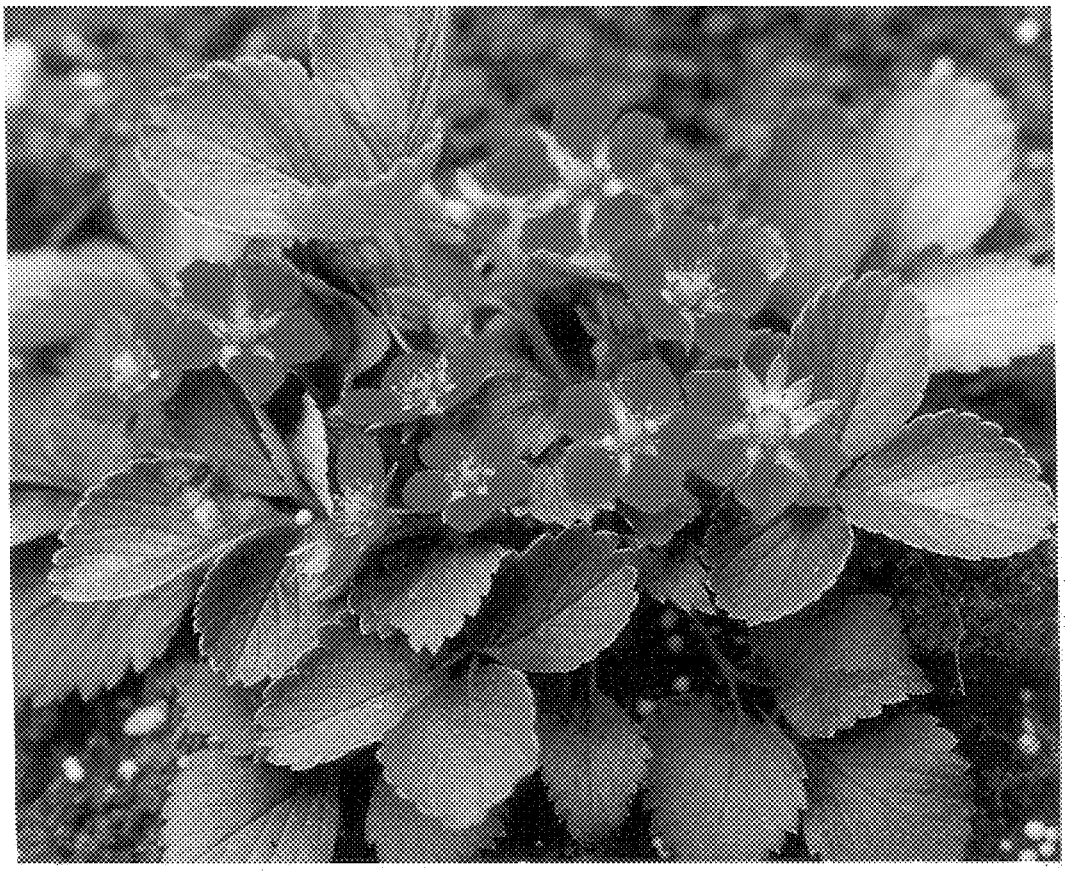

* * * * *